United States Patent
Hayenga et al.

(10) Patent No.: US 7,569,789 B2
(45) Date of Patent: Aug. 4, 2009

(54) CANTILEVERED COAXIAL FLOW INJECTOR APPARATUS AND METHOD FOR SORTING PARTICLES

(75) Inventors: Jon W. Hayenga, Kent, WA (US); Alan C. Nelson, Gig Harbor, WA (US)

(73) Assignee: VisionGate, Inc., Gig Harbor, WA (US)

( * ) Notice: Subject to any disclaimer, the term of this patent is extended or adjusted under 35 U.S.C. 154(b) by 495 days.

(21) Appl. No.: 11/377,032

(22) Filed: Mar. 16, 2006

(65) Prior Publication Data

US 2007/0215528 A1 Sep. 20, 2007

(51) Int. Cl.
*B07C 5/00* (2006.01)
(52) U.S. Cl. ...................... 209/579; 209/576
(58) Field of Classification Search ................ 209/576, 209/579
See application file for complete search history.

(56) References Cited

U.S. PATENT DOCUMENTS

| | | | |
|---|---|---|---|
| 3,560,754 A | 2/1971 | Kamentsky et al. | |
| 4,293,221 A | 10/1981 | Kay | |
| 4,667,830 A | 5/1987 | Nozaki, Jr. | |
| 4,786,165 A | 11/1988 | Yamamoto | |
| 5,144,224 A | 9/1992 | Larsen | |
| 5,726,404 A | 3/1998 | Brody | |
| 5,831,723 A | 11/1998 | Kubota | |
| 5,985,216 A | 11/1999 | Rens | |
| 6,399,177 B1 * | 6/2002 | Fonash et al. | 428/119 |
| 6,431,212 B1 | 8/2002 | Hayenga | |
| 6,540,895 B1 * | 4/2003 | Spence et al. | 204/450 |
| 6,716,629 B2 * | 4/2004 | Hess et al. | 435/420 |
| 6,743,399 B1 | 6/2004 | Weigl | |
| 6,767,706 B2 | 7/2004 | Quake | |
| 6,778,724 B2 * | 8/2004 | Wang et al. | 385/16 |
| 6,833,242 B2 * | 12/2004 | Quake et al. | 435/6 |
| 6,897,015 B2 | 5/2005 | Henderson | |
| 6,935,165 B2 | 8/2005 | Bashir | |
| 6,943,417 B2 | 9/2005 | Boland | |
| 6,949,377 B2 | 9/2005 | Ho | |
| 7,223,371 B2 | 5/2007 | Hayenga | |
| 2002/0008032 A1 | 1/2002 | Hayenga | |
| 2002/0148992 A1 | 10/2002 | Hayenga | |
| 2002/0160518 A1 | 10/2002 | Hayenga | |
| 2003/0175980 A1 | 9/2003 | Hayenga | |
| 2005/0045479 A1 | 3/2005 | Weigl | |

(Continued)

OTHER PUBLICATIONS

Herzenberg, L. A., The History and Future of the Florescence Activated Cell Sorter and Flow Cytometry: A View from Stanford, 2002.

(Continued)

*Primary Examiner*—Patrick H Mackey
*Assistant Examiner*—Terrell H Matthews
(74) *Attorney, Agent, or Firm*—Citadel Patent Law; George A Leone

(57) ABSTRACT

An apparatus and method for sorting particles in a laminar flow microfluidic channel includes a cantilevered coaxial flow injector in a microfluidic device, the cantilevered coaxial flow injector including an elongated cantilever element integrated into the microfluidic device. A coaxial channel runs through the elongated cantilever element, where coaxial channel is sized to pass particles of a predetermined size. An actuator is coupled to the elongated cantilever element, for actuating said elongated cantilever element.

29 Claims, 5 Drawing Sheets

U.S. PATENT DOCUMENTS

| | | |
|---|---|---|
| 2005/0085721 A1 | 4/2005 | Fauver et al. |
| 2005/0129582 A1 | 6/2005 | Breidford |
| 2005/0205816 A1 | 9/2005 | Hayenga |

OTHER PUBLICATIONS

Beckman Coulter,Untitled,Re: The Coulter Principle, US.

Holl et al., Microfluidic Materials: Polymeric Laminate Technology, revised Sep. 7, 2001, http://faculty.washington.edu/yagerp/microfluidicstutorial/polymericlaminates/polymericlaminates.htm, US.

* cited by examiner

CANTILEVERED COAXIAL FLOW INJECTOR APPARATUS AND METHOD FOR SORTING PARTICLES

FIELD OF THE INVENTION

The present invention relates to sorting particles in a laminar flow microfluidic channel and, more particularly, optical cell detection from light scatter, fluorescent tag, or image analysis applied to sorting biological cells in an integrated microfluidic device using an activated cantilevered coaxial flow channel.

BACKGROUND OF THE INVENTION

The use of microfluidic structures in cytometry has rapidly increased with the advent of many microfabrication technologies capable of producing networks of fluidic circuits. Many cytometry applications in microfluidics attempt to differentiate cell types or cells with specific features within a population of cells. The detectors available to classify cells range from light scatter detection, to fluorescence marker, chromatic markers, and morphological image and feature differentiation. Detection necessarily precedes sorting and is followed by a coordinated directing of a cell into one pathway or another. Conventionally, high speed cell sorting fluid droplets that contain the cells of interest are ejected and electrically charged so that they may be electrostatically deflected using a high voltage field to direct the droplets to be collected in one of two locations for further processing.

Sorting cells has many purposes including further study of concentrated cell populations with similar features, such as stem cells or cells with a particular genetic or chemical characteristic that can be marked with fluorescence or stain. Sorting is also an effective means of validating a detection scheme in which a human observation or other reference instrument can evaluate cells with a given detection scheme mechanism or marker.

One sorting technique is found in U.S. Pat. No. 6,778,724, issued Aug. 17, 2004, to Wang et al. entitled, "Optical Switching and Sorting of Biological Samples and Microparticles Transported in a Microfluidic Device, Including Integrated Biochip Devices." There disclosed is a method for switching and sorting small particles pushed with optical pressure forces, with laser light, as arises from VCSELs operating in Laguerre-Gaussian mode, at branching junctions in microfluidic channels so as to enter into selected downstream branches, thereby realizing particle switching and sorting, including in parallel.

Another sorting technique is found in U.S. Pat. No. 6,540,895 issued Apr. 1, 2003, to Spence, et al. entitled, "Microfabricated Cell Sorter for Chemical and Biological Materials." There disclosed is a method for sorting cells into an appropriate branch channel based on the presence or amount of a detectable signal such as an optical signal, with or without stimulation, such as exposure to light in order to promote fluorescence. A thin cantilever may be included within a branch point, such that it may be displaced towards one or the other wall of the main channel, typically by electrostatic attraction, thus closing off a selected branch channel.

Sorting particles, such as cells, in a microfluidic channel takes advantage of the ability to use small fluid sample sizes of less than 1 µL and allows the detection and subsequent separation of sample particles into one of a plurality of possible pathways. The sorting mechanism remains contained and very close to the detection site, thus eliminating the need for long fluidic paths that dilute samples requiring extra processing steps to further concentrate the sample for subsequent detection or analysis.

Another advantage of a microfluidic approach is that sample carryover can be completely eliminated from hardware by providing low cost replacement fluidic pathways for each sample processed. The complexity and uncertainty of cleaning fluidics between sample processing is an often overlooked system detail requiring often 5 to 20 times the fluid flushed through tubing to clean it as it takes to process a sample. Cleaning is further complicated when using microchannels that force laminar flow conditions that eliminate the possibility of creating turbulent shear forces strong enough to clean tubing walls. The only mechanism of removing contamination from tubing walls is diffusion of the wall contaminant into a rinsing solution. Replacing rather than cleaning fluid paths requires less fluid and substantially improves certainty of eliminating sample cross contamination. The primary source of failure in fluidic instrumentation is found in the basic fluidics. Such fluidic failure modes include leaks, clogging, failed seals, biofilm growth, or accumulated contamination. Cleaning solution makes up the overwhelming biowaste volume from instruments such as flow cytometers.

However, until the present invention, no one has contemplated using a laminar flow channel in a microfluidic sorting system including a particle detection system, sorting control and coaxial cantilever injector. The use of the coaxial cantilever injector allows, for the first time, an ability to direct particles, including biological cells, into a selected one of a plurality of strata present in a laminar flow channel. The resultant sorted particles thus comprise an enriched sample for facilitating analysis of disease conditions including various cancers such as lung, colon, prostate, breast, cervical and ovarian cancers.

SUMMARY OF THE INVENTION

The present invention provides an apparatus and method for sorting particles in a laminar flow microfluidic channel using an elongated cantilever element integrated into the microfluidic device. A coaxial channel runs through the elongated cantilever element, where coaxial channel is sized to pass particles of a predetermined size. An actuator is coupled to the elongated cantilever element, for actuating said elongated cantilever element.

DESCRIPTION OF THE PREFERRED EMBODIMENT OF THE INVENTION

Figure 1:
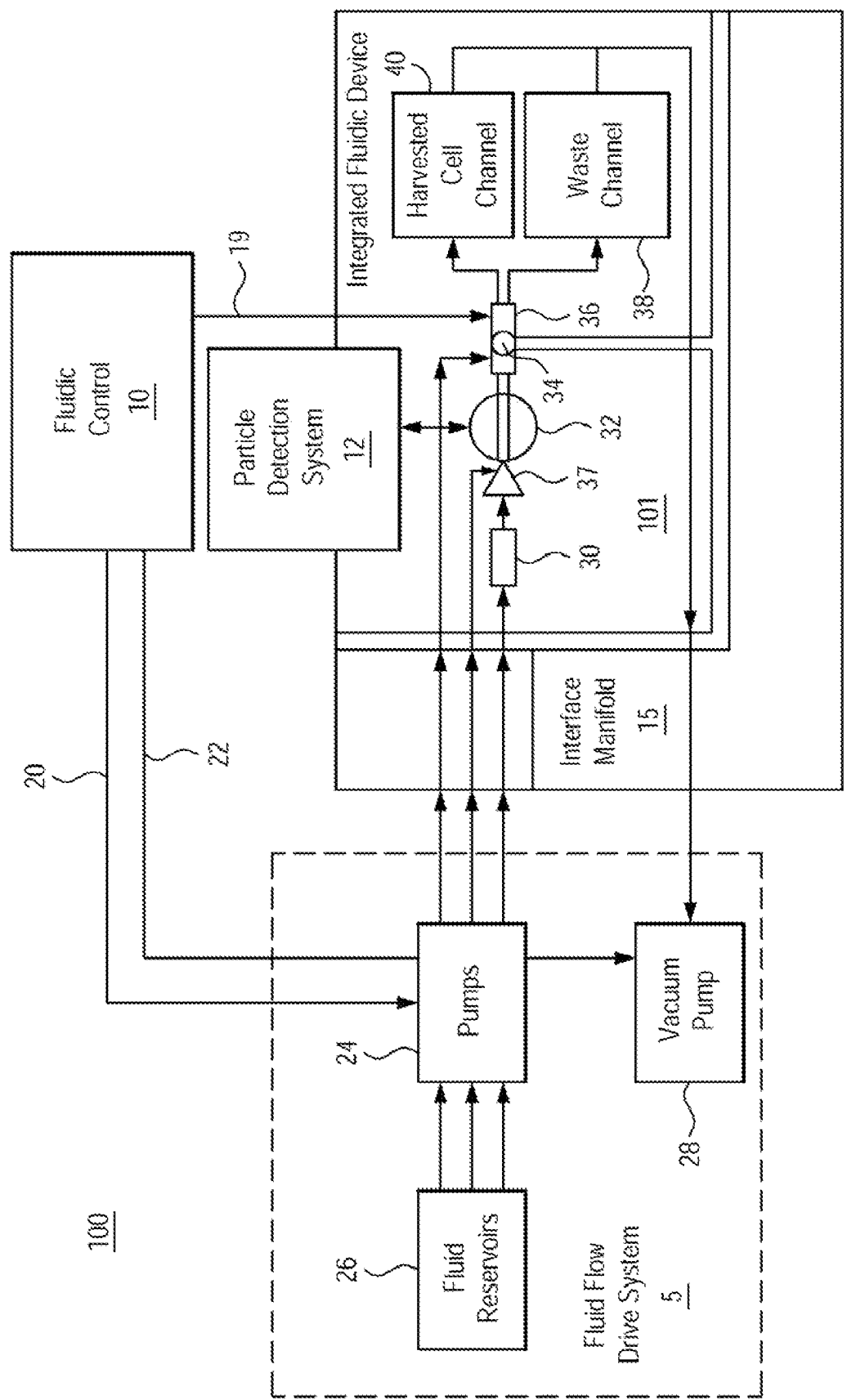
FIG. 1 schematically shows an example block diagram of a system for sorting particles using an activated cantilevered coaxial flow channel as contemplated by one embodiment of the present invention.

The following description is of the best mode presently contemplated for the carrying out of the invention. This description is made for the purpose of illustrating the general principles of the invention, and is not to be taken in a limiting sense. The scope of the invention is best determined by reference to the appended claims.

The system of the present invention takes advantage of laminar flow conditions forced upon the nature of fluid flow at low Reynolds numbers. Laminar flow is defined as flow with Reynolds numbers below 2000, but for most microfluidic applications, especially those using fluids with viscosity larger than water, Reynolds numbers below 20 are nearly always achieved. Low Reynolds number flow assures laminar or layered flow streams in channels. For flow at low Reynolds numbers, movement of fluid orthogonal to the flow direction occurs only when driven by forces other than flow-generated forces. Some possible disruptive forces include diffusion as driven by temperature and molecular weight of fluids, gravitational settling/buoyancy that is a function of weight or density of matter in flow stream, Bernoulli forces including differential pressures created by unequal flow on different sides of an object, and mechanical or electromagnetic forces. For limited distances a particle flowing in a layer of the flow stream will tend to stay in that layer until acted upon by an outside force.

In an exemplary embodiment, the present invention employs a cantilevered coaxial flow injector device that can be bent on command to deliver particles into a particular stratum of a laminar flow stream within a channel. Laminar flow will preserve the location of the injected particle flow stream up to a split in flow path. The fluid path can be split into two or more pathways with symmetrical channel dimensions and material properties so that a near equal split of the flow path occurs. It is often advantageous to evacuate the paths of air to prevent small air entrapments from affecting the symmetry of the laminar flow split.

In operation, actuating or bending the cantilevered centered flow injection tube in a coaxially joined laminar flow path can direct a cell directed to one of two or more channels. The limiting speed of actuation will depend upon the forces applied to cantilever and the natural spring constant of the material used in fabrication, viscous damping of the fluid in the channel, and distance the actuator must travel. In a typical microfluidic channel the deflection required will be less than 100 microns.

The use of a thixotropic or shear thinning solution, such as an optical gel, in a microfluidic device constructed in accordance with the present invention allows for flow in a sorting or detection fluid path to be slowed or stopped without gravitational settling of particles within the fluid. Such solutions further expand the use of a sorter to very slow operation, as, for example sorting particles over a number of hours, without gravitational settling as a limitation. Ready-to-use thixotropic optical gels are selected for their optical properties and optical gels having suitable clarity and refractive indices are commercially available.

Referring now to FIG. 1, an example block diagram of a system for sorting particles in a microfluidic channel as contemplated by one embodiment of the present invention is schematically shown. A sorting system 100 includes a fluidic control system 10 configured to provide a sorting control signal 19, a pump control signal 20 and a vacuum control signal 22. A particle detection system 12 is electronically coupled to transmit imaging information to the fluidic control system 10. A fluid flow drive system 5 receives control information from the pump control signal 20 and the vacuum control signal 22. An interface manifold 15 may also be coupled to the fluid flow drive system 5. An integrated microfluidic device 101 may be mounted in the interface manifold 15. As will be appreciated by those skilled in the art, the interface manifold is not required for every design application of the invention, but may be useful in some applications where replacing fluidics is desired.

The integrated microfluidic device 101 advantageously includes a sample holding channel 30, a hydrodynamic focus cell 37, an inspection zone 32 in communication with a sorting channel 36 including a cantilevered coaxial flow injector 35 (as shown in detail, for example in FIG. 2) downstream of the sample holding channel 30. Through the sorting channel 36 particles, including biological cells, are sorted into at least two output channels including a waste channel 38 and a harvested cell channel 40. The inspection zone 32 is located to pass particles into position to be detected by the particle detection system 12. Where the particle detection system 12 includes a microscope, for example, the inspection zone 32 would be located in the field of view of the microscope optics. In one useful embodiment of the invention a sorting actuator 34 is located proximate the cantilevered coaxial flow injector 35, and coupled to receive the sorting control signal 19 from the fluidic control system 10.

The particle detection system 12 may be any detection system suitable for detecting distinguishing features inherent in or imparted to particles being processed. For example, the particle detection system 12 may be an electrical sensing zone system, a light scatter detection system, a fluorescence based detection system, an optical image capture and processing system, a microscopy system, an optical tomography system or equivalents. The detection system may be external to the microfluidic device, integrated into the microfluidic device or partially integrated into the microfluidic device.

The fluid flow drive system 5 may advantageously include at least one fluid reservoir 26, at least one fluid pump 24 coupled to the at least one fluid reservoir 26 and at least one vacuum pump 28 coupled to the at least one fluid pump 24. Those skilled in the art having the benefit of this disclosure will recognize that the reservoir, vacuum pump and fluid pump may be of differing quantities, sizes and configurations depending on the application so long as they are configured suitably to transmit fluid drive pressure and vacuum pressure to provide laminar flow conditions through the interface manifold to the integrated microfluidic device. The fluid flow drive system may advantageously transmit fluid drive using positive displacement or pressure and/or vacuum pressure to provide laminar flow conditions. In one example embodiment the laminar flow conditions comprise a plug flow using the rheology of shear thinning fluid.

In one useful example embodiment, the sample holding channel 30 contains a biological cell sample. Thus, in the case where particles are being sorted into cells of interest and other particles, the cells of interest may be directed by operation of the sorting actuator to the cell harvest channel 40 while other particles are directed to the waste channel 38. In some applications it may be desirable to further process the unharvested cells into still other particle or cell types. In such cases a plurality of sorting systems of the invention may be connected together to continue sorting based on varying criteria or more than two sorting channels may be employed. Thus the apparatus and method of the invention provide a means for enriching a biological sample so as to facilitate downstream analysis of disease conditions such as cancer.

Depending upon information received from the detection system, the fluidic control system 10 provides a responsive sorting control signal 19 to the sorting actuator 34 that in turn operates to actuate the cantilevered coaxial flow injector 35 to sort biological cells into a selected one of the at least two output channels. For example, in the case where biological cells are being harvested, the cantilevered coaxial flow injector 35 will be actuated to bend to deliver cells of interest into a selected strata of a laminar flow stream leading into the harvest cell channel.

The integrated microfluidic device 101 may comprise a plurality of laminations typical in the construction of microfluidic devices. Various processes are known for producing complex microfluidic systems including chemical wet etching, laser cutting, laminate laser cutting, micromolding, photopolymerization and equivalent methods and combinations of methods. The polymeric laminate process using a multiplicity of layers allows crossover of channels, as well as the potential to use different materials for different layers. Some materials useful for the fabrication of integrated microfluidic devices include silicon, glass, polymeric films, silicone elastomer, photoresist materials, hydrogels, thermoplastics and equivalent known materials.

Figure 2:
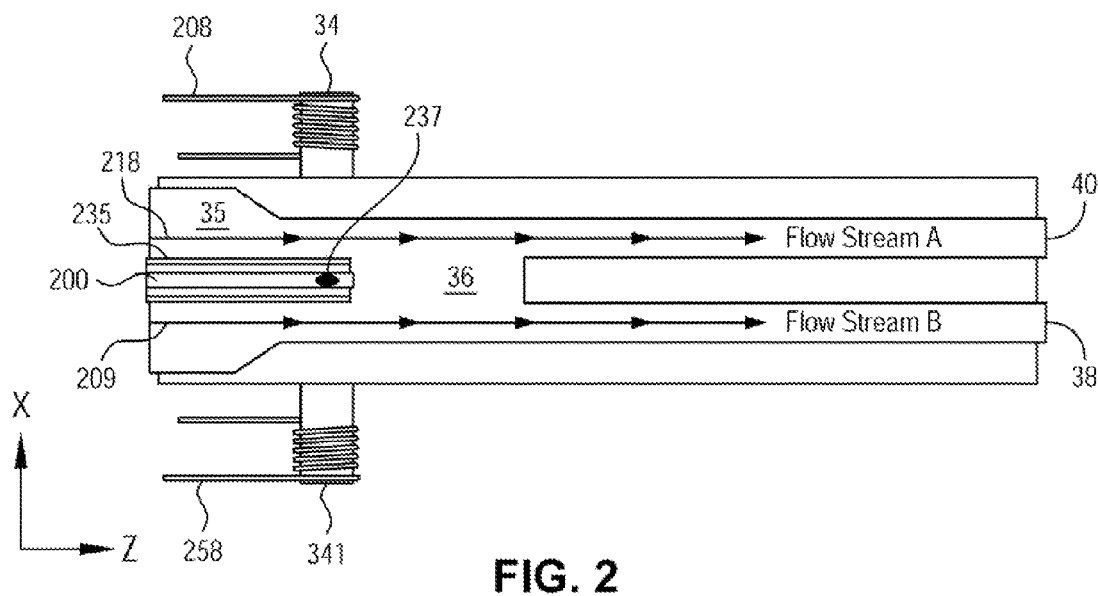
FIG. 2 schematically shows an example illustration of a side view of an integrated microfluidic device for sorting particles in a laminar flow path as contemplated by an embodiment of the present invention.

Referring now to FIG. 2. an example illustration of a side view of an integrated microfluidic device for sorting particles in a laminar flow path as contemplated by an embodiment of the present invention is schematically shown. A cantilevered coaxial flow channel 200 incorporated into the cantilevered coaxial flow injector 35 allows injection of particles or cells into a laminar flow sheath fluid which is split in flow as flow stream 'A', which continues down channel 40 and flow stream 'B', which continues down channel 38. The central channel 200 is cantilevered and suspended into the sheath flow entering channels 218 and 209 from the left. A biological cell 237 or other particle is shown traveling down the cantilevered central channel just before it is ejected into a combined flow area called sorting channel 36. A ferrous coating 235 or embedded ferrous material such as a nickel wire may be embedded into or otherwise applied to the walls of channel 200. Alternatively material 235 may be a bimetallic bender or a piezo bending material to move the cantilevered channel up into flow stream 'A' or down into flow stream 'B'. External to the fluidic channels there may be electromagnetic actuators 34 and 341 that when activated will pull the cantilever toward the actuator. Other equivalent actuation schemes may also be employed.

In one example, the cantilevered coaxial flow injector wherein the coaxial channel may have a diameter in the range of 100 microns to 1 mm. In another example embodiment the cantilevered coaxial flow injector may advantageously have a diameter in the range of 50 microns to 1 mm.

Figure 3:
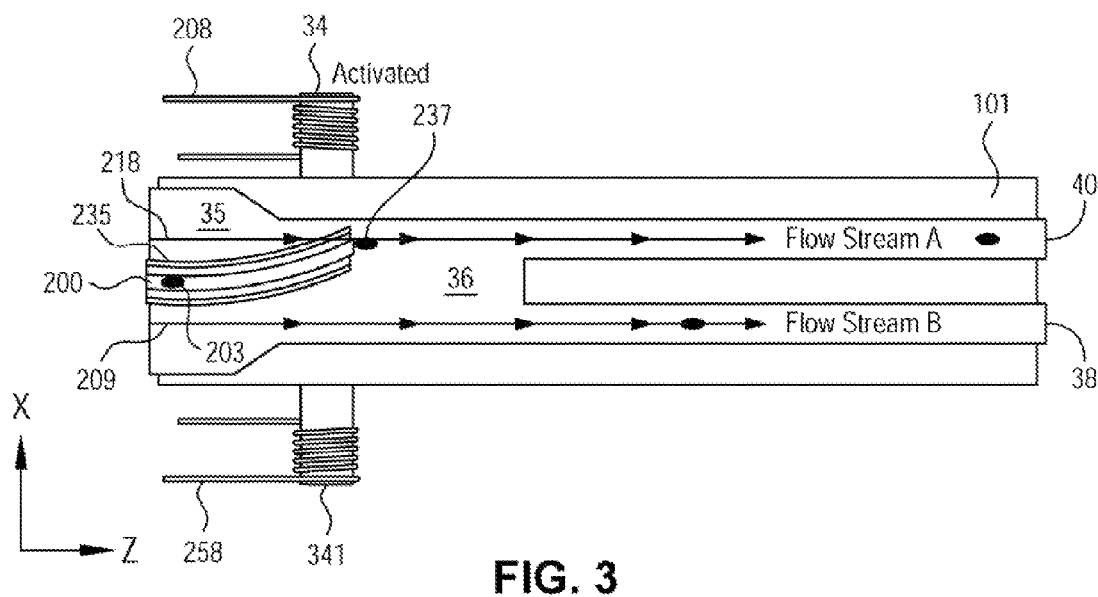
FIG. 3 schematically shows an example illustration of a side view of an integrated microfluidic device in operation for sorting particles in a laminar flow path as contemplated by an embodiment of the present invention.

Referring now also to FIG. 3, an example illustration of a side view of an integrated microfluidic device for sorting particles in a laminar flow path in an actuated state as contemplated by an embodiment of the present invention is schematically shown. In the actuation state shown, a control signal in response to recognition of an object of interest, such as a biological cell 237, causes the first actuator 34 to be activated by an electrical signal at coil 208. In response, the first sorting actuator 34, here an electromagnet, draws cantilevered channel 200 slightly upward in the channel by about 20-100 microns. The slight upward deflection is enough to inject the cell 237 into the laminar flow stream 'A' entering the harvested cell channel 40 from which cells may later be harvested. Because the flow is continuous, the next cell 203 in the central channel 200 will then have to be directed to a selected channel as determined by the particle detection system 12 (FIG. 1) prior to sorting by the cantilevered coaxial flow injector 35. The direction of the next cell 203 will occur by activating either the first actuator 34 or the second actuator 341 with coil 258 after cell 237 has been ejected, but before the next cell 203 reaches the ejection point. Note that if an object of interest is not identified in the inspection area the second sorting actuator 341 would be activated causing the cantilevered coaxial flow injector 35 to bend in the opposite direction thereby directing the uninteresting object into waste channel 38.

Figure 4:
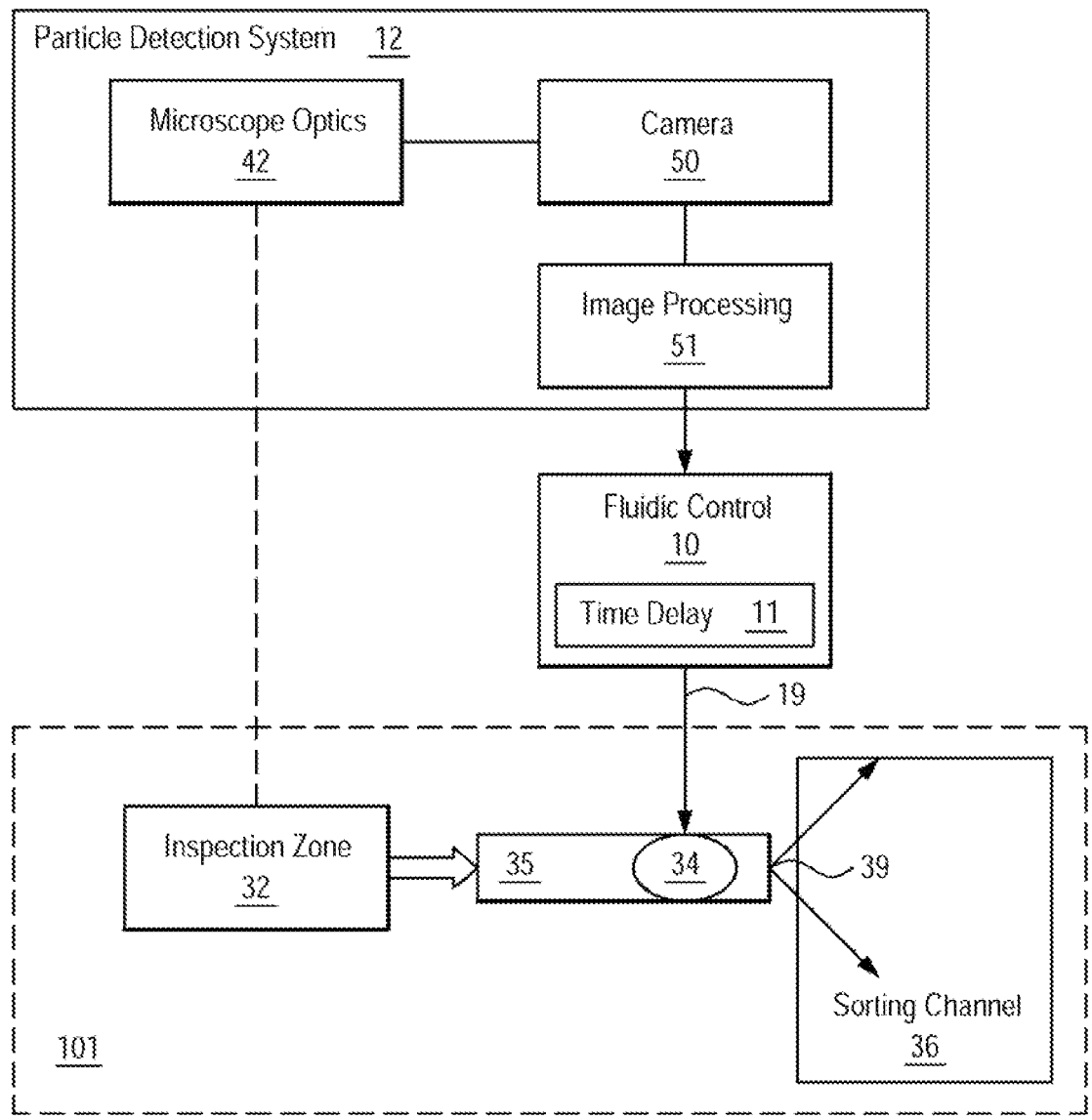
FIG. 4 schematically shows a block diagram of an example embodiment of a detection system as contemplated for use in the present invention.

Referring now to FIG. 4, there shown is one example embodiment of the particle detection system 12 as contemplated for use in the present invention. The particle detection system 12 may advantageously comprise microscope optics 42 coupled to send image information to a camera 50. The camera 50 may advantageously comprise any conventional camera, a digital camera, or equivalent imaging sensor such as one employing charge coupled devices, color, infrared, ultraviolet and other similar sensors depending on the application and spectral frequency being imaged. The camera 50 transmits imaging information to an image processing system 51. The image processing system 51 may advantageously comprise a cell characterization system, a target recognition software program, a single or multidimensional image reconstruction software program or equivalent being run in a personal computer, application specific integrated circuit or equivalent processor. Such software is capable of distinguishing features and characteristics of imaged particles. The image processing system makes a sorting determination based on the image information and transmits the determination to the fluidic control system 10 that generates sorting control signals responsive to images processed in the software program. The fluidic control system may advantageously incorporate a time delay generator 11 for determining the delay between the time that the particle is detected in the inspection zone and the time it reaches the tip 39. The timing mechanism may be a timer incorporated into the fluidic control, or the integrated microfluidic device 101, or added as a separate set of sensors. Alternatively, the time delay may be calculated using known system parameters and the time of detection of a particle or equivalents.

The integrated microfluidic device 101 is positioned so as to locate the inspection zone 32 within the field of view of the microscope optics 42. As the image processing 51 identifies particles and cells from camera images in the inspection zone it sends information to the fluidic control 10. The fluidic control 10, responsively sends a sorting control signal 19 to one of the sorting actuators 34, 341 (341 not shown here). It will be understood that the control signal 19 may represent plurality of analog or digital lines constructed in accordance with accepted engineering principles. That is, if the image processing recognizes a biological cell, for example, the corresponding sorting control signal will actuate the sorting actuators to deflect the cantilever ejector tip 39 to send the cell into the harvested cell channel. If otherwise, the particle will be directed to the waste channel by deflecting the cantilever in the opposite direction.

In one embodiment, the system as contemplated by the present invention may employ optical tomography for the detection system. Some examples of useful optical tomography based systems including reconstruction algorithms are described in U.S. Pat. No. 6,522,775, issued Feb. 18, 2003 to Nelson and entitled, "Apparatus and Method for Imaging Small Objects in a Flow Stream Using Optical Tomography." The full disclosure of U.S. Pat. No. 6,522,775 is incorporated herein by reference.

Figure 5:
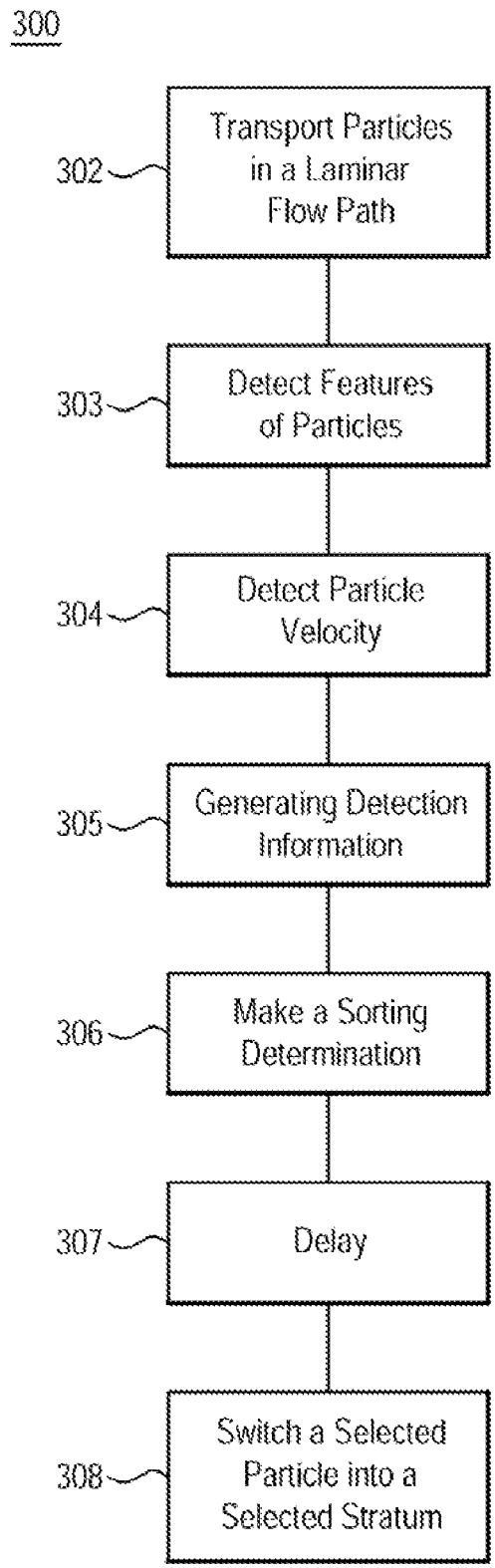
FIG. 5 schematically shows a flow diagram of an example embodiment of a sorting method as contemplated for use in the present invention.

Referring now to FIG. 5, a block diagram of an example embodiment of a sorting method in a microfluidic laminar flow path as contemplated for use in the present invention is schematically shown. The sorting method 300 includes the steps of:

transporting particles in a laminar flow path within an integrated microfluidic device at step 302, detecting features of at least a portion of the plurality of particles in the laminar flow path at step 303, detecting the velocity of said particles with successive images or detections at step 304, generating detection information responsive to the detected features at step 305, making a sorting determination for a selected particle based on the detected features at step 306, delaying until the particle is at the ejector tip at step 307, and directing the selected particle into a selected stratum of the laminar flow path at step 308.

In one useful embodiment the step 302 of transporting particles in a laminar flow path may advantageously be carried out by operating the fluidic control system to provide, a pump control signal and a vacuum control signal and driving fluid flow through an optional interface manifold in response to the pump control signal and the vacuum control signal. In the embodiment using an optical detection system, the step 303 of detecting features of particles in the laminar flow path may advantageously be carried out by capturing images with the camera electronically coupled to the fluidic control system. Microscope optics may be coupled to send images to the camera when samples from a sample holding channel are hydrodynamically focused and transported through the microscope optics field of view and within the optics depth of field. The step 308 of directing the selected particle may advantageously be carried out by the cantilevered coaxial flow injector downstream of the holding sample channel and optical viewing channel. The fluidic control system is operated to provide sorting control signals to the sorting actuator acting on the cantilevered coaxial flow injector in order to direct an object into a laminar flow path, which is split into one of at least two output channels. The step 307 of delaying until the particle is at the ejector tip may advantageously be according to a timed delay determined by measuring or predetermining the velocity of a particle or cell in the flow stream and the distance between the ejector tip and the inspection zone. Thus, the detection of a particle in the inspection zone triggers the time delay. Alternatively, the time delay can be set in other parts of the detection or image processing systems, or combinations thereof.

Figure 6:
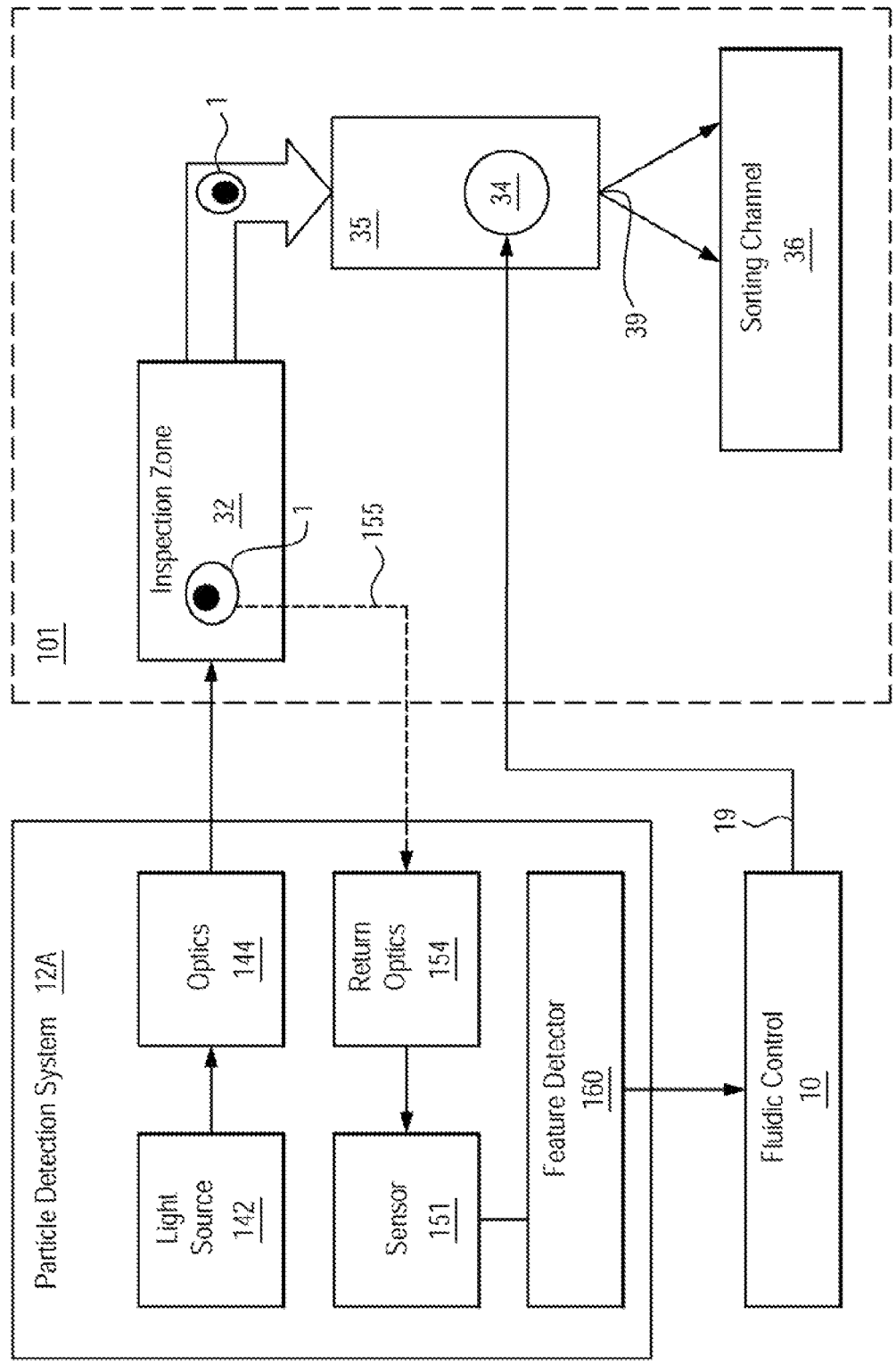
FIG. 6 schematically shows a block diagram of another example embodiment of the particle detection system as contemplated for use in the present invention employing a light scatter detection system

Referring now to FIG. 6, there schematically shown is another example embodiment of the particle detection system 12A as contemplated for use in the present invention. The particle detection system 12A may advantageously comprise a light scatter detection system wherein light may be transmitted from a light source 142 through optics 144 to impinge on a cell 1 in inspection zone 32. Scattered light 155 from the object is transmitted through return optics 154 onto a light sensor 151. Sensing signals from the light sensor are processed by a feature detector 160 which makes a sorting determination based on the scattered light intensity within a given angle of light collection. The feature detector outputs sorting information to the fluidic switch control which responsively actuates the sorting mechanism substantially as described with reference to FIG. 1 through FIG. 6. By substituting sensors and light sources as is within the skill of those in the art having the benefit of this disclosure, a similar detection system may be used to detect fluorescence or spectrally coded signals from the object where color or presence of spectrally coded biomarker are input into the decision to direct a particle or cell into one channel or another, in this example, cell 1.

Although specific embodiments of the invention have been described herein with reference to the drawings, it should be understood that such embodiments are by way of example only and are merely illustrative of the many possible specific embodiments to which the principles of the invention may be applied. Various changes and modifications obvious to one skilled in the art to which the invention pertains are deemed to be within the spirit, scope and contemplation of the invention as further defined in the appended claims.

What is claimed is:

1. A cantilevered coaxial flow injector in a laminar flow microfluidic device comprising:
    an elongated cantilever element integrated into said laminar flow microfluidic device;
    a coaxial channel running through said elongated cantilever element, said coaxial channel being sized to pass particles of a predetermined size; and
    an actuator, coupled to said elongated cantilever element, for actuating said elongated cantilever element so as to deliver the particles into a selected strata in fluid communication with one of at least two output channels without closing a channel.

2. The cantilevered coaxial flow injector of claim 1 wherein said actuating means comprises an actuator selected from the group consisting of a piezoelectric bending device, a magnetic field generator, an electromagnetic element, and an electrostatic attraction device.

3. The cantilevered coaxial flow injector of claim 1 wherein the elongated cantilever element incorporates at least one of a wire, a ferrous coating, imbedded ferrous material, and a nickel wire.

4. The cantilevered coaxial flow injector of claim 1 wherein the coaxial channel is sized to pass biological cells in a laminar flow.

5. The cantilevered coaxial flow injector of claim 1 wherein the elongated cantilever element is adapted to be actuated to dispense particles into a plurality of laminar flow strata in the microfluidic device.

6. The cantilevered coaxial flow injector of claim 1 wherein the coaxial channel has a diameter in the range of 100 microns to 1 mm.

7. The cantilevered coaxial flow injector of claim 1 wherein the coaxial channel has a diameter in the range of 50 microns to 1 mm.

8. A system for sorting particles in microfluidic channels, the system comprising:
    a particle detection system for generating detection information;
    a fluidic control system electronically coupled to the particle detection system, the fluidic control system configured to provide a sorting control signal responsive to information received from the particle detection system;
    a fluid flow drive system coupled to the fluidic control system;
    a microfluidic device including a sample holding channel, an inspection zone, a cantilevered coaxial flow injector downstream of the inspection zone and at least two output channels, wherein the cantilevered coaxial flow injector includes an elongated cantilever element with a coaxial channel running through said elongated cantilever element, said coaxial channel being sized to pass particles of a predetermined size; and a sorting actuator coupled to receive the sorting control signal, the sorting actuator being located to actuate the cantilevered coaxial flow injector so as to deliver the particles into a selected strata in fluid communication with one of at least two output channels without closing a channel.

9. The system of claim 8 further comprising a hydrodynamic focus cell coupled to transmit particles to the inspection zone, where the hydrodynamic focus cell centers the particles.

10. The system of claim 8 wherein the particle detection system is selected from the group consisting of an electrical sensing zone system, a light scatter detection system, a fluorescence detection system, an optical spectral detection system, an optical image capture and processing system, a microscopy system, and an optical tomography system.

11. The system of claim 8 wherein the fluid flow drive system comprises at least one fluid reservoir, at least one fluid pump coupled to the at least one fluid reservoir and at least one vacuum pump coupled to the fluid pump and the microfluidic channels.

12. The system of claim 8 wherein the fluid flow drive system transmits fluid drive using positive displacement or pressure and/or vacuum pressure to provide laminar flow conditions.

13. The system of claim 12 wherein the laminar flow conditions comprise a plug flow.

14. The system of claim 8 wherein the particles comprise biological cells.

15. The system of claim 8 wherein the sorting control signal actuates the cantilevered coaxial flow injector to sort biological cells into a selected one of the at least two output channels.

16. The system of claim 15 wherein the cantilevered coaxial flow injector bends to deliver particles into a selected stratum of a laminar flow stream within a selected one of the at least two output channels.

17. The system of claim 8 wherein the sorting actuator is selected from the group consisting of a piezoelectric bending device, a magnetic field generator, an electromagnet, and an electrostatic attraction device.

18. The system of claim 8 wherein the cantilevered coaxial flow injector incorporates at least one of a wire, a ferrous coating, imbedded ferrous material, and a nickel wire.

19. A method for sorting particles in a microfluidic laminar flow path, the sorting method comprising the steps of:

transporting a plurality of particles in a laminar flow path within an integrated microfluidic device;

detecting features of the plurality of particles in the laminar flow path;

generating detection information responsive to the detected features;

making a sorting determination for a selected particle based on the detection information;

injecting the selected particle into a cantilevered coaxial flow injector downstream of the holding sample channel, wherein the cantilevered coaxial flow injector includes an elongated cantilever element with a coaxial channel running through said elongated cantilever element, said coaxial channel being sized to pass particles of a predetermined size; and providing sorting control signals responsive to the sorting determination to a sorting actuator acting on the cantilevered coaxial flow injector in order to direct the selected particle into a selected stratum of the laminar flow path through one of at least two output channels so as to deliver the selected particle into a selected strata in fluid communication with one of at least two output channels without closing a channel.

20. The method of claim 19 wherein the step of transporting further includes hydrodynamically focusing the plurality of particles in the laminar flow path.

21. The method of claim 19 wherein the step of detecting features comprises operating at least one of a light scatter detection system to detect features including scattering properties, a fluorescence detection system to detect features including fluorescence properties, a microscopy system for detecting features including imaging properties, and an optical image capture, an optical tomography system for detecting features including imaging properties, and processing system for detecting features including imaging properties.

22. The method of claim 21 wherein the step of operating an optical image capture and processing system comprises the step of capturing images of particles in the laminar flow path with a camera.

23. The method of claim 21 wherein the optical image capture and processing system further comprises a target recognition software program for making the sorting determination.

24. The method of claim 19 wherein the step of transporting particles in a laminar flow path comprises operating a fluidic control system to provide a pump control signal and a vacuum control signal and using a fluid drive system to drive fluid flow.

25. The method of claim 19 wherein the cantilevered coaxial flow injector bends to deliver particles into the selected stratum of a laminar flow stream.

26. The method of claim 19 wherein the sorting actuator is selected from the group consisting of a piezoelectric bending device, a magnetic field generator, an electromagnet, and an electrostatic attraction device.

27. The method of claim 19 wherein the cantilevered coaxial flow injector incorporates at least one of a wire, a ferrous coating, imbedded ferrous material, and a nickel wire.

28. The method of claim 19 wherein the particles comprise biological cells.

29. The cantilevered coaxial flow injector of claim 1 wherein the laminar flow microfluidic device comprises a microfluidic chip.

\* \* \* \* \*